United States Patent
Martins et al.

(10) Patent No.: US 10,695,553 B2
(45) Date of Patent: Jun. 30, 2020

(54) BIOMEDICAL ELECTRODE COMPRISING DISCONTINUOUS PRIMER LAYER

(71) Applicant: 3M INNOVATIVE PROPERTIES COMPANY, St. Paul, MN (US)

(72) Inventors: Fernanda Martins, São Paulo (BR); Roberta K. Sadi, São Paulo (BR); Jener de Oliveira, São Paulo (BR)

(73) Assignee: 3M Innovative Properties Company, St. Paul, MN (US)

( * ) Notice: Subject to any disclaimer, the term of this patent is extended or adjusted under 35 U.S.C. 154(b) by 77 days.

(21) Appl. No.: 15/528,566

(22) PCT Filed: Dec. 10, 2015

(86) PCT No.: PCT/US2015/064995
§ 371 (c)(1),
(2) Date: May 22, 2017

(87) PCT Pub. No.: WO2016/105965
PCT Pub. Date: Jun. 30, 2016

(65) Prior Publication Data
US 2017/0281926 A1    Oct. 5, 2017

Related U.S. Application Data

(60) Provisional application No. 62/095,236, filed on Dec. 22, 2014.

(51) Int. Cl.
*A61N 1/04* (2006.01)
*A61B 5/0408* (2006.01)
(Continued)

(52) U.S. Cl.
CPC ........ *A61N 1/0496* (2013.01); *A61B 5/04087* (2013.01); *A61N 1/046* (2013.01);
(Continued)

(58) Field of Classification Search
CPC .......................... A61N 1/0496; A61B 5/04087
See application file for complete search history.

(56) References Cited

U.S. PATENT DOCUMENTS

RE24,906 E    12/1960  Ulrich
2,973,826 A    3/1961  Barnhart
(Continued)

FOREIGN PATENT DOCUMENTS

EP    0051935    11/1986
FR    2755372    5/1998
(Continued)

OTHER PUBLICATIONS

Rao, "Polylysine-Modified PEG-Based Hydrogels to Enhance the Neuro-Electrode Interface," Journal of Biomaterial Science, 2011, vol. 22, pp. 611-625.
(Continued)

*Primary Examiner* — William J Levicky (57) ABSTRACT

Articles and methods of making articles are described. In one embodiment, an electrode is described, comprising an ionically-conductive hydrogel layer comprising a first major surface and opposing major surface. The electrode further comprises a discontinuous primer layer disposed on the first major surface ionically-conducting hydrogel layer and an electrically conductive member or a connector component thereof, in contact with the first major surface of the ionically-conducting hydrogel layer. In another embodiment, an article is described comprising a hydrogel layer comprising a first major surface and opposing major surface; a discontinuous hydrophobic primer layer disposed on the first hydrogel layer; and a hydrophobic adhesive or hydrophobic backing bonded to the primer and discontinuous hydrophobic primer layer of the hydrogel.

21 Claims, 2 Drawing Sheets

(51) Int. Cl.
*C09J 7/30* (2018.01)
*C09J 7/21* (2018.01)

(52) U.S. Cl.
CPC ......... *A61N 1/0456* (2013.01); *A61N 1/0492* (2013.01); *C09J 7/21* (2018.01); *C09J 7/30* (2018.01); *A61B 2562/125* (2013.01); *C09J 2433/00* (2013.01); *C09J 2483/00* (2013.01)

(56) References Cited

U.S. PATENT DOCUMENTS

| | | | |
|---|---|---|---|
| 3,389,827 A | 6/1968 | Abere | |
| 3,645,835 A | 2/1972 | Hodgson | |
| 4,051,842 A * | 10/1977 | Hazel | A61B 5/0408 600/391 |
| 4,112,213 A | 9/1978 | Waldman | |
| 4,310,509 A | 1/1982 | Berglund | |
| 4,323,557 A | 4/1982 | Rosso | |
| 4,406,827 A | 9/1983 | Carim | |
| 4,554,924 A | 11/1985 | Engel | |
| 4,595,001 A | 6/1986 | Potter | |
| 4,732,808 A | 3/1988 | Krampe | |
| 4,848,353 A * | 7/1989 | Engel | A61B 5/04087 600/391 |
| 4,917,928 A | 4/1990 | Heinecke | |
| 4,917,929 A | 4/1990 | Heinecke | |
| RE33,353 E | 9/1990 | Heinecke | |
| 5,223,569 A | 6/1993 | Schmid | |
| 5,338,490 A * | 8/1994 | Dietz | A61B 5/04087 252/500 |
| 5,489,624 A | 2/1996 | Kantner | |
| 5,520,683 A | 5/1996 | Subramaniam | |
| 5,674,561 A | 10/1997 | Dietz | |
| 5,924,983 A | 7/1999 | Takaki | |
| 5,928,142 A * | 7/1999 | Cartmell | A61B 5/04087 600/372 |
| 6,038,464 A * | 3/2000 | Axelgaard | A61B 5/04087 600/391 |
| 6,064,908 A | 5/2000 | Muller | |
| 6,709,716 B2 | 5/2004 | Uy | |
| 7,620,439 B2 | 11/2009 | Menon | |
| 7,999,023 B2 | 8/2011 | Menon | |
| 8,541,481 B2 | 9/2013 | Determan | |
| 2003/0088239 A1 * | 5/2003 | Takaki | A61B 5/04087 606/1 |
| 2003/0199745 A1 | 10/2003 | Burson | |
| 2007/0032719 A1 * | 2/2007 | Menon | A61B 5/04087 600/391 |
| 2009/0227857 A1 | 9/2009 | Rowe | |
| 2011/0212325 A1 | 9/2011 | Determan | |
| 2013/0023816 A1 | 1/2013 | Bachinski | |

FOREIGN PATENT DOCUMENTS

| | | |
|---|---|---|
| WO | WO 1997-034947 | 9/1997 |
| WO | WO 1999-039635 | 8/1999 |
| WO | WO 2000-006215 | 2/2000 |
| WO | WO 2000-046319 | 8/2000 |
| WO | WO 02/087645 A1 | 11/2002 |
| WO | WO 2007-041158 | 4/2007 |
| WO | WO 2007-092290 | 8/2007 |

OTHER PUBLICATIONS

Technical Data Sheet, Mod. DT0104E—Primer EPA W 5, ICHEMCO srl, Dec. 2014, 1 page.
Technical Data Sheet, Mod. DT0104E—Primer EPA W 8, ICHEMCO srl, Mar. 2014, 1 page.
Technical Data Sheet, Mod. DT0104E—Primer EPA W, ICHEMCO srl, Sep. 2011, 1 page.
Woolfson, "Moisture-activated, Electrically Conducting Bioadhesive Interfaces for Biomedical Sensor Applications", Analyst, Jun. 1996, vol. 121, pp. 711-714.
International Search Report for PCT International Application No. PCT/US2015/064995, dated Mar. 9, 2016, 6 pages.

* cited by examiner

BIOMEDICAL ELECTRODE COMPRISING DISCONTINUOUS PRIMER LAYER

CROSS REFERENCE TO RELATED APPLICATIONS

This application is a national stage filing under 35 U.S.C. 371 of PCT/US2015/064995, filed Dec. 10, 2015, which claims the benefit of U.S. Provisional Application No. 62/095,236, filed Dec. 22, 2014, the disclosure of which is incorporated by reference in its/their entirety herein.

SUMMARY

In one embodiment, an electrode is described comprising an ionically-conductive hydrogel layer comprising a first major surface and opposing major surface. The electrode further comprises a discontinuous primer layer disposed on the first major surface ionically-conducting hydrogel layer and an electrically conductive member or a connector component thereof, in contact with the first major surface of the ionically-conducting hydrogel layer. In some embodiments, the electrode further comprises a backing comprising a pressure sensitive adhesive. The pressure sensitive adhesive is bonded to the electrically conductive member or a connector component thereof. The pressure sensitive adhesive is also bonded to the discontinuous primer layer and portion of the first major surface of the hydrogel layer. In another embodiment, the backing is bonded to the discontinuous primer layer and portion of the first major surface of the hydrogel layer.

In another embodiment, an article is described comprising a hydrogel layer comprising a first major surface and opposing major surface; a discontinuous hydrophobic primer layer disposed on the first hydrogel layer; and a hydrophobic adhesive or hydrophobic backing bonded to the primer and discontinuous hydrophobic primer layer of the hydrogel.

Also described is a method of making an article comprising applying an water-based primer composition comprising a hydrophobic polymeric material to a first surface of a hydrogel; removing water from the primer composition to form a discontinuous primer layer; and bonding a backing or a pressure sensitive adhesive disposed on the backing to the opposing surface of the discontinuous primer and hydrogel.

When the article is an electrode, an electrically conductive member is disposed between the hydrogel and backing or disposed between the hydrogel and pressure sensitive adhesive.

DETAILED DESCRIPTION

With reference to FIG. 1-4, the biomedical electrode comprises an ionically conductive hydrogel layer 55 comprising a first major surface 56 and an opposing major surface 57. The opposing major surface 57 of the ionically conductive hydrogel layer 55 is the skin-contacting surface of the biomedical electrode during use. The ionically conductive hydrogel layer 55 is typically disposed upon release liner 12 at the time of use. The biomedical electrode further comprises a discontinuous primer layer 52 disposed on the first major surface 56 of ionically-conductive hydrogel composition 55. A (e.g. two-part) electrically conductive member (e.g. 51A and 51B) is disposed upon and in electrical connection with ionically conductive hydrogel layer 55. In some embodiments, the electrically conductive member, such as connector component 51B, may be embedded within the ionically conductive hydrogel layer 55. The electrically conductive connector component 51B may be characterized as a male terminal or male pin of a two-part electrically conductive member.

Figure 1:
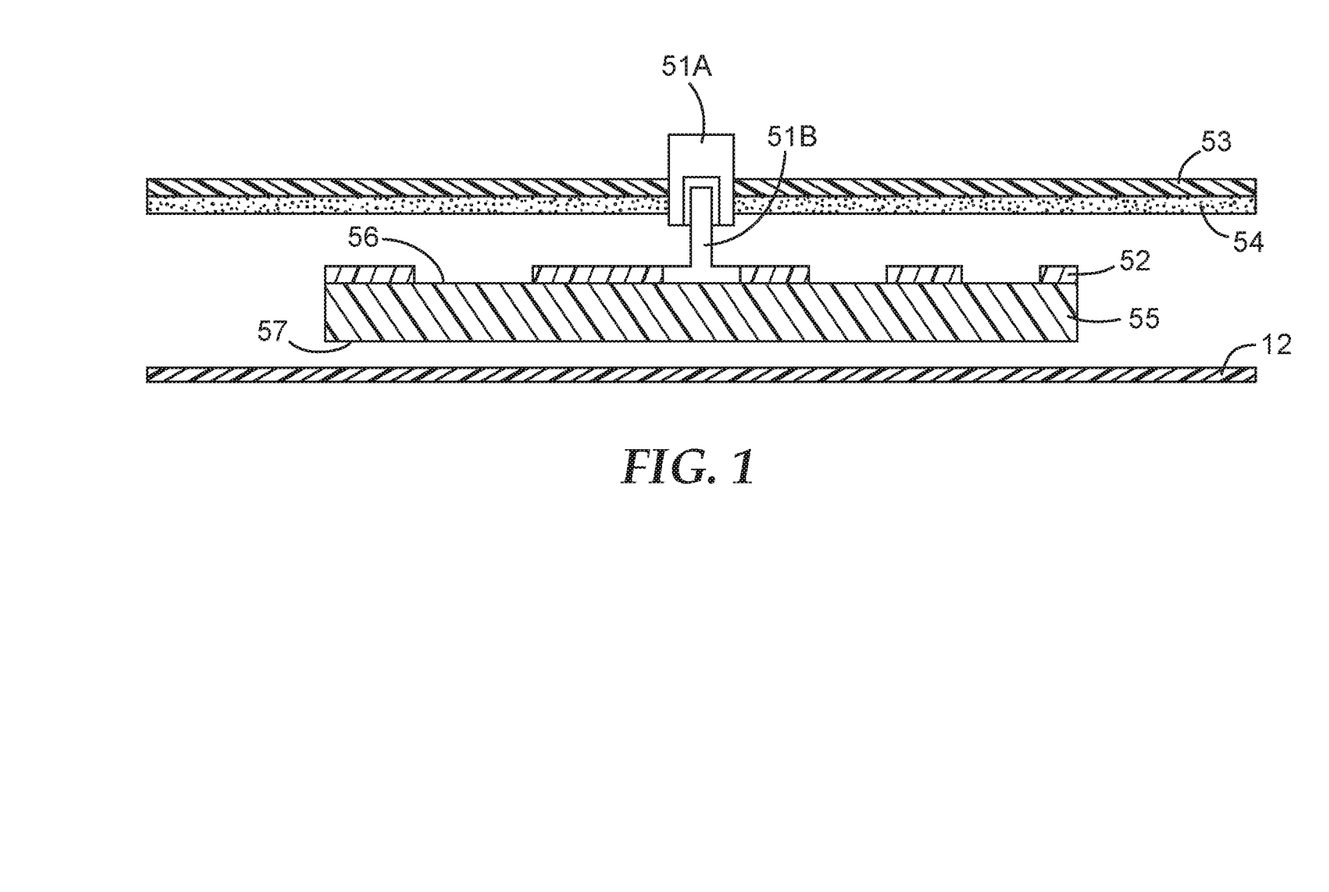
FIG. 1 is a cross-sectional view of an illustrative biomedical electrode.
Figures 2, 3:
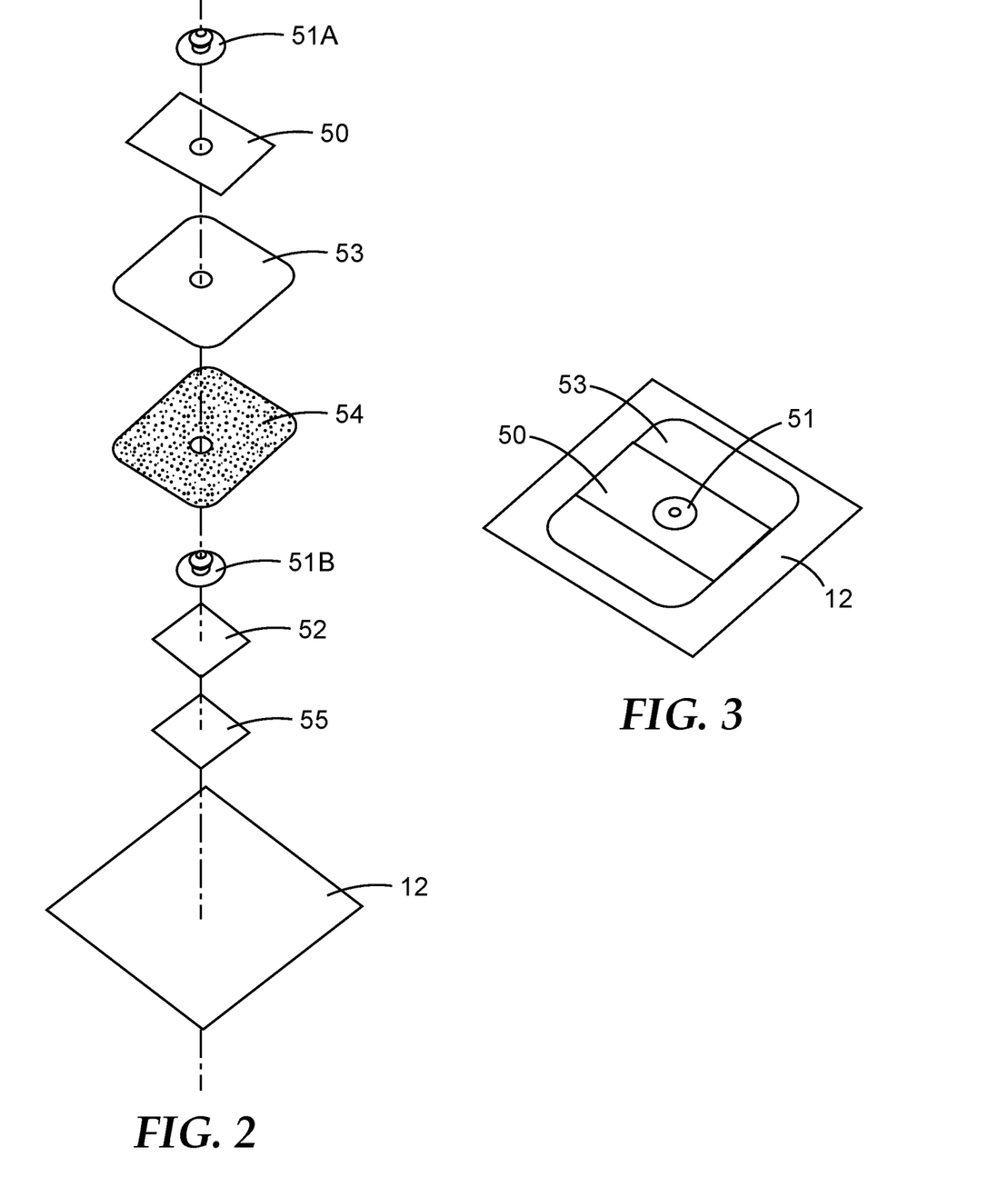
FIG. 2 is an exploded schematic view of an illustrative biomedical electrode
FIG. 3 is a top plan view of an illustrative biomedical electrode.

In typical embodiments, the biomedical electrode further comprises a backing 53 and a pressure sensitive adhesive 54. The pressure sensitive adhesive 54 is bonded to the top surface of electrically conductive member, such as connector component 51B. The top surface is the opposing surface relative to the surface that is in contact with the hydrogel. Disposing the electrically conductive member, such as connector component 51B, between the hydrogel 55 and backing 53 by means of pressure sensitive adhesive 54 contributes to securing the electrically conductive member or connector component thereof e.g. 51B in place. The pressure sensitive adhesive 54 of the backing 53 is also bonded to the discontinuous primer layer 52 wherein the primer layer is outside the area occupied electrically conductive member or connector component thereof (e.g. 51B). The primer is typically discontinuously distributed over the total first major surface 56 of the hydrogel and not only the surface area outside area of the conductive member 51B. Due to the fact that primer layer 52 is discontinuous, discrete portions of the underlying ionically-conductive hydrogel composition 55 are not covered by the primer layer and thus are exposed. The exposed portions of the ionically-conductive hydrogel composition 55 are in contact with pressure sensitive adhesive 54.

In one embodiment, (not shown) the ionically conductive hydrogel layer 55 is approximately the same size (e.g. length, width, shape) as the pressure sensitive adhesive 54 and backing 53 such that pressure sensitive adhesive 54 contacts the ionically conductive hydrogel layer 55, yet does not contact release liner 12. In more typical embodiments, are shown in FIGS. 1-2 the ionically conductive hydrogel layer 55 is smaller is size than pressure sensitive adhesive 54 and backing 53. In this embodiment, the peripheral area of the pressure sensitive adhesive 54 is a biomedical pressure sensitive adhesive that functions to bond the biomedical electrode to the skin during use.

In the case of two-part electrically conductive members, connector component 51A may be at least partially positioned within aperture 58 of backing 53 and pressure sensitive adhesive 54 and mechanically couples with connector component 51B.

In typical embodiments, second connector component 51B is also electrically conductive. The second connector component 51B may be characterized as a female receptacle which receives male terminal or pin of first connector component 51B in a snap-type or threaded relation therewith to couple components 51A and 51B with one another. Other arrangements for coupling first and second connector components 51A, 51B are also envisioned including "pinch clip" arrangements, "twist on" couplings or the like. It is also envisioned that second connector component 51B may include the male pin or terminal and first connector component 51B may include the associated female receptacle to receive the male terminal to couple the components. Further, it is also possible to have a one piece electrically conductive member such as first connector component 51B in the absence of second connector components 51A.

In typical embodiments, the electrically conductive member is a two-part conductive member comprising a metallic stud 51A joined to an eyelet 51B. Various metallic studs and eyelets are commercially available. For example, stainless steel eyelets, such as No. 304, are commercially available from companies such as Eyelets for Industry of Thomaston, Conn. Further plastic, metallic plated eyelets, such as an poly(acrylonitrile butadiene styrene) ("ABS") plastic eyelet plated with a silver compound, such as silver chloride is commercially available from Micron Products of Fitchburg, Mass.

In an alternate embodiment, if connector component 51B is non-conductive, an electrical interface may be established via electrically conductive connector component 51A and a non-conductive connector member 51B. Electrically conductive connector component 51A is thus in electrical contact with ionically conductive hydrogel layer 55 via connector component 51B.

During use, 51A in electrical contact with 51B (in the case of two-part electrically conductive members) or 51B alone (in the case of one-part electrically conductive members) are connected to a terminal of biomedical device such as an electrocardiogram (ECG) electrode or a transcutaneous electrical nerve stimulation (TENS) electrode. The electrically conductive members may be in the form of a suitable style connector adapted to mechanically and electrically couple with a complementary terminal (not shown) of a biomedical device.

Biomedical electrode is typically provided with a release liner 12 to cover ionically conductive hydrogel layer 55 and in typical embodiments, peripheral biomedical pressure sensitive adhesive layer 54. Non-limiting examples of suitable release liners commercially available include silicone coated polyethylene terephthalate films commercially available from H. P. Smith Co. and fluoropolymer coated polyester films commercially available from 3M Company as "ScotchPak" brand release liners.

The biomedical electrode may comprise other optional components (not shown). In some embodiments, additional layers are disposed on backing 53. For example, the backing may further comprise a label 50. In some embodiments, additional layers are disposed between the second major surface of the ionically conductive hydrogel and the backing 53. For example, a scrim (e.g. woven and/or nonwoven cloth) 205 may be embedded within or supporting the structure of the ionically conductive hydrogel layer 55 conductive composition (e.g., hydrogel).

Various ionically conductive hydrogels composition can be utilized. Both synthetic and natural hydrogels can be utilized herein. Illustrative specific types can include those found in U.S. Pat. Nos. 4,848,353; 4,406,827; 6,038,464; 4,554,924; 5,489,624; 6,709,716; and 7,999,023 for example, the disclosures of which are incorporated herein by reference thereto.

In one embodiment, the ionically conductive hydrogels composition comprises an adhesive copolymer matrix (e.g. formed by free radical polymerizing an adhesive precursor) comprising a carboxylic acid as a water-soluble hydrogen bond donating monomer, a water-soluble hydrogen bond accepting monomer (e.g. N-vinyl pyrrolidone). The molar ratio of hydrogen bond accepting sites to hydrogen bond donating sites available on the monomers typically ranges from about 1:3 to about 6:1. Further, the weight ratio of carboxylic acid to N-vinyl pyrrolidone typically ranges from about 1:2 to about 3:1.

The adhesive further comprises a plasticizing, electrically-conductive solution. Such solution typically comprises 0 to 98% by weight water-soluble, polar organic compound, about 2 to 100% by weight water, and about 0 to 12% by weight water-soluble salt. The adhesive composition comprises at least 10 or 15% (e.g. 12%) up to about 50% by weight non-volatile copolymer matrix. The hydrogen bond donating sites on the copolymer matrix are from about 5% to about 80% neutralized. The composition is substantially homogeneous and pressure-sensitive adhesive.

The copolymer matrix is preferably covalently cross-linked and the adhesive precursor further comprises a multifunctional crosslinker present up to about 2.5% by weight of the total monomers in the adhesive precursor.

The hydrogen bond donating monomer is selected from the group of carboxylic acids consisting of alpha, beta.-ethylenically unsaturated carboxylic acids having up to eight carbon atoms. The hydrogen bond donating monomer may comprise acrylic acid at an amount of about 15% to about 25% by weight of the copolymer matrix. The hydrogen bond accepting monomers include any polymerizable monomer having at least one hydrogen bond accepting group. N-vinylpyrrolidone, N-vinyl amides, N-vinyl lactams and alpha, beta-unsaturated amides such as acrylamide or substituted acrylamides may be used.

The plasticizing electrically-conductive solution is "electrically-conductive" when it contains polar or ionic species effective to provide sufficient electrical conductivity in the final composition for the intended use. The solution may contain from 0% to 98%, and in some embodiments at least 34, 40 or 50% by weight water-soluble, polar organic compound. The polar organic compound may be a polyhydric alcohol monomer or polymer. Low molecular weight polyoxyethylene glycols are suitable (average M.W. 200 to 600 e.g., Carbowax™. 200 and 600 available from Union Carbide). Glycerol is preferred. The plasticizing electrically-conductive solution may also contain from 2% to 100% water. Additionally the solution may contain up to 12% by weight of soluble salt as previously described.

One suitable electrically-conductive adhesive is made from an adhesive precursor having by weight 10% acrylic acid (50% neutralized with sodium hydroxide), 10% N-vinyl-pyrrolidine, 0.125% TEGBM, 0.07% benzildimethylketal (Irgacure™651, Ciba Giegy), 1% potassium chloride 25.5% water and 53.5% glycerol.

Other exemplary hydrogels include, for example the hydrogel adhesive of AG603-6 sensing gel (available from AmGel Technologies a division of Axelgaard Manufacturing Company Ltd. Of Fallbrook, Calif.), COMFORT GEL A027 (M842) (available from R&D Medical Products Inc., Lake Forest, Calif., USA) and the hydrogel adhesive of 3M™ RED DOT™ Resting EKG Electrode 2330 (3M, St. Paul, Minn.).

In another embodiment, the hydrogel may comprise a multi-layer structure such as described in U.S. Pat. No. 6,038,464. The ionically conductive multi-layer hydrogel includes a first layer having a relatively low peel strength that removably adheres to a patient's skin. The first, or skin contact layer may be soft, with a wet feeling and have an affinity for skin adhesion while at the same time enabling easy separation, or peeling from the skin. The second layer has a relatively high peel strength for contacting the conductive member, the pressure sensitive adhesive of the backing layer, or the backing itself. In some embodiments, the first and second layer of the multi-layer hydrogel are bonded to each other by means of a third layer.

The first and second layer may generally comprise the same components as previously described, i.e. an adhesive copolymer matrix comprising a carboxylic acid (such as acrylic acid) as a water-soluble hydrogen bond donating monomer, a water-soluble hydrogen bond accepting monomer (such as N-vinyl pyrrolidone), a plasticizing electrically-conductive solution (comprising glycerol), and multifunctional crosslinker. In some embodiments, the ionically conductive multi-layer hydrogel further comprises a thickener.

To tailor the differing characteristics of the first and second layer, the first layer may comprise more glycerol than the second layer. In addition, the first layer may comprise less soluble hydrogen bond accepting monomer (e.g. N-vinylpyrrolidone) than the second layer. Further, the first and second layers may utilize different multifunctional crosslinkers. In some embodiments, a scrim layer disposed between the first and second layers and laminated therebetween in order to modify or control the physical characteristics of the combined first and second layer.

The discontinuous primer layer 52 generally comprises an electrically insulating polymeric material. Since the polymeric material of the primer layer is electrically insulating, it generally reduces the conductivity relative to the same construction in the absence of the primer. However, due to the fact that the primer layer is discontinuous, the primer layer comprises a plurality of discrete portions wherein the primer material is present defined by an adjacent area or discrete portions wherein the primer is absent. In some embodiments, the discontinuous primer layer generally includes a (e.g. continuous) matrix where there is no primer material surrounding the discrete portions. Without intending to be bound by theory, the discrete portions where the primer material is present improves the adhesion to the pressure sensitive adhesive of the backing or improves the adhesion to the backing itself. Concurrently, the matrix surrounding the discrete portions of primer material provides direct contact between the conductive member and the ionically conducting hydrogel.

When the matrix lacking primer material surrounding the discrete portions of primer material is of sufficient surface area, the conductivity is minimally reduced such that the electrode passes conductivity testing according to the AAMI/ANSI EC12 standard and preferably the limit ranges set forth in the examples. Thus, there is a synergistic balance of improved adhesion in combination with high conductivity.

Surprisingly, very small amounts of primer can improve the adhesion. The mass/per area of dried polymer material disposed on the first surface of the hydrogel) is typically at least 0.001, 0.0015, 0.002, 0.0025, 0.003, or 0.0035 g/sqm. In some embodiments, the mass/per area is no greater than 30, 25, 20, or 15 g/sqm. Depending on the selection of primer and hydrogel, a concentration of 15 g/sqm and greater can begin to cause failures under at least some testing conditions.

The total surface area that comprises the discrete portions of primer material can vary. In typical embodiments, at least 5, 10, 15 or 20% of the surface area of the first major surface of the ionically conductive hydrogel comprises the discrete portions of primer material. Further, in some favored embodiments, no greater than about 60, 55, 50, 45, or 40% of the surface area of the first major surface of the ionically conductive hydrogel comprises the discrete portions of primer material.

The primer material is hydrophobic, especially with respect to the hydrogel. The suitability of a primer can be evaluated by applying a small amount of an water-based (e.g. water-borne) primer solution to a hydrogel of interest, and removing the water from the water-based primer solution, such as by drying. The resulting surface can then be stained and inspected via microscopy. When the primer material is sufficiently hydrophobic relative to the hydrogel, the dried primer material does not form a continuous coating on the hydrogel. Rather the primer separates into discrete (e.g. irregular shaped) portions. The size of the discrete portions can vary. In some embodiments, the discrete portions of primer (when inspected in top plan view under a microscope) range in size from about 25 microns to about 100 microns and greater. Further, more than one (e.g. irregular shaped) discernible portion can be contacting another portion such that the total discrete portion of primer has a maximum dimension up to 500 microns or greater.

Various commercially available compositions are suitable for use as the primer material such as various water-based dispersions and emulsions of hydrophobic polymeric materials such as poly(meth)acrylate (i.e. acrylic resins), polyurethanes, polyolefins, and the like. By water-based it is meant that the liquid medium of the emulsion or dispersion comprises or consists of water and optionally small concentrations of organic solvent(s). Unlike the hydrogel, the primer material after drying comprises little or no water (e.g. less than 5, 4, 3, 2, or 1 wt-%). In some embodiments, such hydrophobic polymeric materials may be characterized as film-forming resins since when applied to a typical hydrophobic polymeric materials rather than hydrogels, such emulsion and dispersions do form a continuous film. Some representative suitable primer compositions include waterborne polymers available from Ichemco, Milano, Italy as further described in the examples.

In one embodiment, the method of making the biomedical electrode or intermediate construction thereof generally comprises applying a water-based primer comprising a e.g. (electrically-insulating) hydrophobic polymeric material to a first surface of a hydrogel. The water-based primer composition is typically applied such that mass per area of the dried primer is within the ranges previously described. Following applying the water-based primer, the method comprises removing water from the emulsion such as by absorbing at least a portion of the water into the hydrogel, evaporating a least a portion of the water, or a combination thereof. After removing sufficient amounts of water the hydrophobicity of the polymeric material causes the primer to separate such that polymeric material of the primer is present as a plurality of discrete portions, the discrete portions defined by adjacent areas wherein the primer is absent.

After removing the water, the method comprises bonding a backing or a pressure sensitive adhesive disposed on the backing to the opposing surface of the electrically conductive member, discontinuous primer and hydrogel.

Although applying a water-based hydrophobic polymer to the hydrogel is a preferred method of making the biomedical electrode or intermediate article thereof, there are others ways of applying a discontinuous coating such as known in the art. For example, the primer could be pattern coated onto the hydrogel by use of a mask. This could be beneficial to insure that the presence of the discrete primer portions are uniform throughout the first major surface of the hydrogel.

The biomedical electrode typically comprises a backing 53 covering the first major surface of the hydrogel. In some embodiments, the backing material is typically hydrophobic relative to the hydrogel. In this embodiment, upon drying the water-based primer composition forms a continuous film on the backing material. In some embodiments, the backing material has a high moisture vapor transmission rate such as for use in medical tapes, dressings, bandages, and the like. Suitable backing materials nonwoven, foam, and films such as disclosed in U.S. Pat. Nos. 3,645,835 and 4,595,001, the disclosures of which are incorporated by reference. Other examples of a variety of films commercially available as extrudable polymers include "Hytrel 4056" and "Hytrel 3548" branded polyester elastomers available from E. I. DuPont de Nemours and Company of Wilmington, Del., "Estane" branded polyurethanes available from B.F. Goodrich of Cleveland, Ohio or "Q-thane" branded polyurethanes available from K.J. Quinn & Co. of Maiden, Mass.

In some embodiments, the backing 53 may directly contact the first major surface of the ionically conducting hydrogel. In this embodiment, the ionically conducting hydrogel is preferably the previously described multi-layer construction in order that the layer in contact with the backing provides adequate adhesion.

In another embodiment, the backing 53 further comprises a pressure sensitive adhesive layer 54. In some embodiments, the pressure sensitive adhesive is hydrophobic relative to the hydrogel. In this embodiment, upon drying the water-based primer composition forms a continuous film on the pressure sensitive adhesive. In this embodiment, pressure sensitive adhesive 54 is typically not conductive.

In one embodiment, the pressure sensitive adhesive layer 54 of the backing 53 has a size and shape such that the pressure sensitive adhesive layer 54 contacts the conductive member, and hydrogel, but does not comes in contact with skin during use. In this embodiment, various acrylic pressure sensitive adhesives can be utilized such as generally described in U.S. Pat. Nos. 2,973,826; Re 24,906; Re 33,353; 3,389,827; 4,112,213; 4,310,509; 4,323,557; 4,732,808; 4,917,928; 4,917,929; and European Patent Publication 0 051 935, all incorporated herein by reference.

In one embodiment, pressure sensitive adhesive 54 comprises an adhesive copolymer having from about 95 to about 97 weight percent isooctyl acrylate and from about 5 to about 3 percent acrylamide. The pressure sensitive adhesive 54 may have inherent viscosity of 1.1-1.25 dl/g is presently preferred.

In another embodiment, backing 53 and pressure sensitive adhesive layer 54 have a greater surface area than the first major surface of the hydrogel. In this embodiment, pressure sensitive adhesive layer 54 contacts the conductive member, the hydrogel, and contacts the patient's skin during use. In this embodiment, pressure sensitive adhesive layer 54 is a biomedical skin adhesive. Various biomedical skin adhesive are known including the high adhesion acrylic hydrogel as previously described.

In another embodiment, pressure sensitive adhesive layer 54 may comprise a silicone adhesive.

Silicone gel adhesives provide good adhesion to skin with gentle removal force and have the ability to be repositioned. Examples of commercially available silicone gel adhesive systems include products marketed with the trade names: Dow Corning MG 7-9850, WACKER 2130, BLUESTAR 4317 and 4320, and NUSIL 6345 and 6350.

These gentle skin adhesives are formed by an addition cure reaction between vinyl-terminated poly(dimethylsiloxane) (PDMS) and hydrogen terminated PDMS, in the presence of a hydrosilation catalyst (e.g., platinum complex). Vinyl-terminated and hydrogen terminated PDMS chains are referred to as 'functionalized' silicones due to their specific chemical moieties. Individually, such functional silicones are generally not reactive; however, together they form a reactive silicone system. Additionally, silicate resins (tackifiers) and PDMS with multiple hydrogen functionalities (crosslinkers) can be formulated to modify the adhesive properties of the gel.

The silicone gel adhesives resulting from the addition cure reaction are very lightly crosslinked polydimethysiloxane (PDMS) networks with some level of free (not crosslinked) PDMS fluid and little or no tackifiying resin.

In another embodiments, the silicone adhesive may comprise a radiation cured silicone gel, wherein the silicone gel comprises a crosslinked poly diorganosiloxane material, a non-crossedlinked polydiorganosiloxane fluid, and a silicate resin tackifier as described in U.S. Pat. No. 8,541,481.

EXAMPLES

The invention is further illustrated by the following non-limiting examples, in which all parts are by weight unless otherwise stated.

TABLE 1

Hydrogels, Primers, and Test Tape

| Component ID | Description, Trade Name and Source |
|---|---|
| HG1 | Hydrogel: AG603-6 sensing gel (AmGel Technologies, a division of Axelgaard Manufacturing Company Ltd. of Fallbrook, CA) |
| HG2 | Hydrogel: COMFORT GEL A027 part number HG2, (R&D Medical Products Inc., Lake Forest, CA, USA) |
| P1 | Primer: Water-borne emulsion of polyolefin polymers, EPA W (ICHEMCO, Cuggiono, Milano, Italy) |
| P2 | Primer: Water-borne emulsion of acrylic polymers, EPA W5 (ICHEMCO) |
| P3 | Primer: Water borne emulsion of polyurethane, EPA W8 (ICHEMCO) |
| T1 | Test Tape: VENTURETAPE 7132M-HC is a 0.8 mm) (1/32 inch) white polyethylene foam tape coated with a high tack medical grade acrylic adhesive, (Venture Tape Corp. Rockland, MA, USA) |

The hydrogels used in the EXAMPLES were composed basically of polyacrylic acid, glycerin and potassium chloride and are supplied with two release liners. A polyethylene release liner with thicknesses of 0.05 mm (0.002 inch) is applied to hydrogel side 1. A polyester release liner with thickness 0.127 mm (0.005 inch) is applied to hydrogel side 2. Table 2 shows a summary of the properties of the primers and the hydrogels used in the EXAMPLES. Unless otherwise described, the primer was applied on the first side of the hydrogel. The primer solutions were diluted in distilled water using different ranges as shown in more details below.

TABLE 2

Properties of Primers and Hydrogels

| Material | Property | Unit | Value |
|---|---|---|---|
| Primer P1 | Total Solids | % | 30 ± 1 |
| | Brookfield Viscosity at 25° C. | cps | 50-100 |
| Primer P2 | Total Solids | % | 50 ± 1 |
| | Brookfield Viscosity at 25° C. | Cps | 100-500 |
| | pH | — | 7.5-8.5 |
| Primer P3 | Total Solids | % | 40 ± 1 |
| | Brookfield Viscosity at 25° C. | cps | 20-90 |
| | pH | — | 7-8.5 |

TABLE 2-continued

Properties of Primers and Hydrogels

| Material | Property | Unit | Value |
|---|---|---|---|
| HG1 | Max. Volume Resistivity | ohm.cm | 1000 |
|  | Thickness | mm | 0.64 ± 0.1 |
| HG2 | Max. Volume Resistivity | ohm.cm | 1500 |
|  | Thickness | mm | 0.69 ± 0.1 |

Sample Preparation

Method 1: Primer Application to Hydrogel Side 1.

a) Primer solution was weighed and diluted with deionized water to the desired concentration.

b) The polyethylene release liner was removed from side 1 of the hydrogel.

c) Diluted primer was applied to surface of side 1 of the hydrogel by transferring it with a Pasteur pipette onto the hydrogel side 1 and spreading the primer with a spatula. Each drop was dispersed in a rectangular shaped area of approximately 31 mm×20 mm;

d) The hydrogel containing the primer was dried for 5 minutes inside an oven at 55° C.

e) The polyethylene release liner was reapplied to side 1 of the hydrogel and left for one day at room temperature conditions.

f) The next day the polyethylene release liner was removed again from side 1 of the hydrogel.

g) The release liner was removed from the test foam tape T1 and the tape was laminated onto side 1 of the hydrogel (roll weight pressure of 2.4 Kg was applied to the hydrogel).

The hydrogels laminated to the T1 were allowed to stand for 1 day at room temperature conditions.

h) The following day, the Adhesion Test was performed between the test foam tape T1 and the Example hydrogel.

i) For Electrical Testing, (see below) a piece of hydrogel containing the primer was laminated onto a partially preassembled electrode where the hydrogel completely covers the eyelet and partially covers the adhesive of the foam tape T1.

Variations to Method 1:

1. Control No Primer (samples with no primer solution added): omit steps a), b), c), d), e) and in step i) the hydrogel did not contain the primer.
2. Control with Water (samples with water used instead of primer): steps a), c), d) and i) the primer was replaced by deionized water in the same total weight of diluted primer solution added.

Adhesion Test

After preparation of the samples, the peel adhesion of the hydrogel to the test foam tape was evaluated by using the IMASS SP-2000 Slip/Peel Tester (available from IMASS Inc. of Accord, Mass., USA), speed 30 cm/min, roll weight for hydrogel pressure 2.4 kg, weight used in the machine 5 kg and 20 seconds of testing. Six measurements were performed for each formulation. A modified version of ASTM D3330 Standard "Test Method for Peel Adhesion of Pressure-Sensitive Tape" was performed for 180° degree peel adhesion testing. One side of double sided adhesive tape was adhered to the steel plate and the hydrogel was affixed to the other side of the double sided adhesive tape. The foam test tape, T1, which was laminated to the hydrogel, was pulled by the IMASS SP-2000 Slip/Peel Tester.

Electrical Testing

Prepared biomedical electrodes (BME) samples containing the hydrogel with and without the primer were also tested for their electrical properties in order to see if the primer disturbed the conductivity of the electrodes. BME samples were assembled using the same component materials from 3M Brazil electrode 2223BRQ (tape used was VENTURETAPE 7132M-HC is a (1/32 inch) (0.8 mm) white polyethylene foam tape coated with a high tack medical grade acrylic adhesive, available from Venture Tape Corp. Rockland, Mass., USA); see FIG. 2 for an exploded view of an example electrode assembly, which was practiced in the EXAMPLES. The XTRATEK II ECG Electrode Tester (product of Xtratek of Lenexa, Kans., USA) was used to perform ACZ (Alternating Current Impedance), DCO (Direct Current Offset), SDR (Simulated Defibrillation Recovery), Noise and Bias analysis, following the testing methods described in the AAMI/ANSI EC12 standard. The following preferred electrical testing results were imposed as the PASS requirements: DCO<10 mV, ACZ<1300 ohm, SDR<25 mV, slope 1.0 mV/s, Noise<150 µV and Bias<100.0 mV.

Example 1

Following METHOD 1, Primers P1, P2, and P3 were added to hydrogel side 1 of HG1 and HG2 using three different concentrations as detailed in TABLE 3. Adhesion Test results are summarized in TABLE 4.

TABLE 3

EXAMPLE 1 SAMPLE PREPARATIONS

| Hydrogel | Primer Variable | Quantity of primer added (dry weight basis - grams per square meter) | | |
|---|---|---|---|---|
|  |  | A | B | C |
| HG1 | Control no primer | None | | |
|  | Control with water | None | | |
|  | Primer |  |  |  |
|  | P3 | 0.75 | 1.5 | 3.0 |
|  | P1 | 0.75 | 1.5 | 3.0 |
|  | P2 | 0.75 | 1.5 | 3.0 |
| HG2 | Control no primer | None | | |
|  | Control with water | None | | |
|  | Primer |  |  |  |
|  | P3 | 0.75 | 1.5 | 3.0 |
|  | P1 | 0.75 | 1.5 | 3.0 |
|  | P2 | 0.75 | 1.5 | 3.0 |

TABLE 4

EXAMPLE 1 ADHESION RESULTS

| Primer on HG2 | Adhesion of HG2 to acrylic adhesive (T1) (gf/19 mm) | Primer on HG1 | Adhesion of HG1 to acrylic adhesive (T1) (gf/19 mm) |
|---|---|---|---|
| Control no primer | 56.7 ± 8.1 | Control no primer | 178.7 ± 10.5 |
| Control with water | 63.8 ± 18.8 | Control with water | 250.0 ± 32.7 |
| P3-A | 122.3 ± 14.5 | P3-A | 421.4 ± 23.2 |
| P3-B | 132.8 ± 4.7 | P3-B | 412.1 ± 10.2 |
| P3-C | 142.5 ± 9.1 | P3-C | 293.1 ± 29.8 |
| P1-A | 382.2 ± 21.6 | P1-A | 463.8 ± 20.0 |
| P1-B | 380.9 ± 16.8 | P1-B | 454.5 ± 25.7 |
| P1-C | 362.6 ± 37.9 | P1-C | 414.8 ± 22.9 |
| P2-A | 184.8 ± 7.5 | P2-A | 427.4 ± 20.6 |
| P2-B | 224.0 ± 20.8 | P2-B | 377.6 ± 53.4 |
| P2-C | 268.3 ± 21.6 | P2-C | 404.1 ± 31.8 | gf = gram force

Example 2

EXAMPLE 2 was performed using Method 1 to apply Primer P2 to hydrogel HG2 to define a minimum and maximum acceptable levels of primer that would work for both adhesion and electrical properties. Primer P2 was applied in amounts of 0.15 grams and 15 grams dry primer per square meter. The results are summarized in TABLE 5. Note that even at the lowest level (0.15 g/sqm) of primer applied in EXAMPLE 2, which is 1/10th of the recommended quantity suggested by the supplier, there is still an increase in the adhesion. Additionally, the EXAMPLE 2 samples adequately passed the electrical tests, even though some individual prepared samples did not; see TABLE 6, ET-2.

The EXAMPLE 2 samples with 15 g/sqm Primer P2 on the HG2 hydrogel were further examined using a Leica, Model DFC295 optical microscope, to assess the physical condition of the primer on the hydrogel. For better visibility the primer on the hydrogel was viewed after treatment with blue dye: Blue Vitasyn AE-90 from Clariant (0.1% w/w), and yellow dye: Vitasyn Chinolin Yellow 70 from Clariant (0.1% w/w). It was observed that indeed the primer formed into agglomerations, discreet areas primer, which were a discontinuous layer on top of the hydrogel. The total surface area of the hydrogel that was covered by the primer material was about 60%.

TABLE 5

ADHESION TEST RESULTS OF EXAMPLE 2

| Samples | Control without water | Control with water | Dry basis primer weight 0.15 g/sqm | Dry basis primer weight 15 g/sqm |
|---|---|---|---|---|
| Adhesion on acrylic adhesive T1 (gf/19 mm) | 128.6 ± 17.8 | 122.3 ± 8.5 | 166.2 ± 13.9 | 279.1 ± 20.2 |
| Electrical test ID | — | ET-1 (TABLE 6) | ET-2 (TABLE 6) | ET-3 (TABLE 6) |

TABLE 6

ELECTRICAL RESULTS OF EXAMPLE 2

| | 12 pairs tested | | | | | | | 1 pair | 1 pair |
|---|---|---|---|---|---|---|---|---|---|
| Samples* | 1st DCO | 1st ACZ | 1st SDR | 2nd SDR | 3rd SDR | 4th SDR | 2nd ACZ | tested Noise | tested Bias |
| ET-1 - a | Pass | Pass | Pass | Pass | Pass | Pass | Pass | Pass | Pass |
| ET-1 - b | Pass | Pass | Pass | Pass | Pass | Pass | Pass | Pass | Pass |
| ET-2 - a | Pass | Pass | Pass | Pass | Pass | Pass | Pass | Pass | Pass |
| ET-2 - b | Pass | Pass | Pass | Pass | Pass | Pass | Pass | Pass | Pass |
| ET-3 - a | Pass | Pass | Fail (1 pair) | Fail (1 pair) | Fail (1 pair) | Fail (1 pair) | Pass | Pass | Pass |
| ET-3 - b | Pass | Pass | Pass | Fail (1 pair) | Fail (1 pair) | Fail (1 pair) | Pass | Pass | Pass |
| ET-3 - c | Pass | Pass | Fail (2 pairs) | Fail (2 pairs) | Fail (2 pairs) | Fail (2 pairs) | Pass | Pass | Pass |

Pass = all 12 pairs passed.
Fail (X) = number of pairs of electrodes/12 pairs that failed.
*letters a, b and c refer to different replicates of the same sample

Example 3

EXAMPLE 3 was performed using Method 1 to apply Primer P2 to hydrogel HG2 to further explore the minimum acceptable level of primer that would work for adhesion. The assumption was that electrical properties would not be negatively affected by less primer. Therefore, no electrical testing was performed on EXAMPLE 3. An amount of 0.037 grams dry primer/sqm of hydrogel was applied to the hydrogel according to METHOD 1 and tested according to the ADHESION TEST. The results from are summarized in TABLE 7.

TABLE 7

ADHESION TEST RESULTS OF EXAMPLE 3

| | Primer P2 on HG2 hydrogel | | |
|---|---|---|---|
| Samples | Control no water | Control with water | Dry basis primer weight 0.0037 g/sqm |
| HG2 Adhesion to acrylic adhesive T1 (gf/19 mm) | 95.9 ± 10.2 | 108.5 ± 5.0 | 154.7 ± 12.2 |

Example 4 Hydrogel with Various Primers Laminated to Silicone Adhesive

A silicone adhesive similar to as that which is provided on 3M™ Spunlaced Polyester Nonwoven Silicone Adhesive Tape 2476, available from 3M Company of St. Paul, Minn. was evaluated with the three primers. The primers P1, P2, and P3 were added onto side 1 of the HG2 hydrogel at a concentration of 1.5 grams dry primer/sqm according to METHOD 1, and laminated to the foam backing of tape T1, but with the silicone adhesive described above, used instead of the acrylic adhesive previously used. Results are shown in TABLE 8. An increase in the hydrogel-to-tape adhesion was observed for the three primers evaluated.

TABLE 8

ADHESION TEST RESULTS OF EXAMPLE 4

| Samples | Control No Primer | Control with water | P1 on HG2 gel | P2 on HG2 gel | P3 on HG2 gel |
|---|---|---|---|---|---|
| HG2 Adhesion to silicone adhesive (gf/19 mm) | 216.0 ± 11.6 | 210.0 ± 14.9 | 292.8 ± 28.8 | 332.3 ± 42.5 | 266.6 ± 45.3 |

Various modifications and alterations of this invention will become apparent to those skilled in the art without departing from the scope and spirit of this invention.

What is claimed is:

1. An electrode comprising:
   a) an ionically-conductive hydrogel layer comprising a first major surface and opposing major surface;
   b) a discontinuous primer layer disposed on the first major surface ionically-conducting hydrogel layer, wherein the discontinuous primer layer comprises a plurality of discrete portions where primer is absent, wherein the discontinuous primer layer is disposed on the hydrogel at an amount ranging from 0.03 to 15 grams per square meter; and
   c) an electrically conductive member or a connector component thereof, in contact with the first major surface of the ionically-conducting hydrogel layer.

2. The electrode of claim 1 further comprising a backing comprising a pressure sensitive adhesive wherein the pressure sensitive adhesive is bonded to the electrically conductive member or a connector component thereof, the discontinuous primer layer, and portion of the first major surface of the hydrogel layer.

3. The electrode of claim 2 wherein the backing comprises a nonwoven or foam material.

4. The electrode of claim 2 wherein the electrically conductive member or a connector component thereof, extends through the backing.

5. The electrode of claim 2 wherein the pressure sensitive adhesive comprises an acrylic polymer or silicone polymer.

6. The electrode of claim 1 further comprising a backing bonded to the discontinuous primer layer and discrete portion of the first major surface of the hydrogel layer.

7. The electrode of claim 6 wherein the hydrogel has a multi-layer structure including a first layer that removable adheres to skin and a second layer having a higher peel strength than the first layer, and the second layer is bonded to the backing.

8. The electrode of claim 1 wherein the primer layer comprises a polymeric material that is electrically-insulating.

9. The electrode of claim 1 wherein the primer comprises a hydrophobic polymeric material.

10. The electrode of claim 9 wherein hydrophobic polymeric material is selected from polyurethane, polyolefin, or polyacrylate.

11. The electrode of claim 1 wherein the hydrogel comprises at least 50 wt-% of polar liquid medium comprising water and at least 10 wt-% of a crosslinked hydrophilic polymer.

12. The electrode of claim 11 wherein the hydrogel comprises an ionically disassociated salt.

13. The electrode of claim 1 wherein the hydrogel is a biocompatible pressure sensitive adhesive.

14. The electrode of claim 1 further comprising a release liner disposed on the opposing major surface of the ionically-conducting hydrogel layer and optionally the peripheral area of the pressure sensitive adhesive.

15. The electrode of claim 1, wherein the discontinuous primer layer includes a continuous matrix of primer and the plurality of discrete portions.

16. The electrode of claim 1, wherein the total surface area of the plurality of discrete portions is at least 5% of the surface area of the first major surface.

17. The electrode of claim 1, wherein a discrete portion from the plurality of discrete portions has a dimension of at least 25 microns.

18. An article comprising:
   a) a hydrogel layer comprising a first major surface and opposing major surface;
   b) a discontinuous hydrophobic primer layer disposed on the first hydrogel layer, wherein the discontinuous primer layer comprises a continuous matrix of a plurality of discrete portions where the primer is absent, wherein the discontinuous primer layer is disposed on the hydrogel at an amount ranging from 0.03 to 15 grams per square meter; and c) a hydrophobic adhesive or hydrophobic backing bonded to the primer and discontinuous hydrophobic primer layer of the hydrogel.

19. A method of making an article comprising:
a) applying an water-based primer composition comprising a hydrophobic polymeric material to a first surface of a hydrogel;
b) removing water from the primer composition to form a discontinuous primer layer, wherein the discontinuous primer layer comprises a plurality of discrete portions where the primer is absent, and wherein the discontinuous primer layer is disposed on the hydrogel at an amount ranging from 0.03 to 15 grams per square meter; and
c) bonding a backing or a pressure sensitive adhesive disposed on the backing to the opposing surface of the discontinuous primer and hydrogel.

20. The method of claim 19 wherein an electrically conductive member is disposed between the hydrogel and backing or pressure sensitive adhesive.

21. The method of claim 19 wherein removing water from the primer composition comprises absorbing at least a portion of the water into the hydrogel, removing water comprises evaporating a least a portion of the water, or a combination thereof.

* * * * *